US008585613B2

(12) United States Patent
Nagano et al.

(10) Patent No.: US 8,585,613 B2
(45) Date of Patent: Nov. 19, 2013

(54) GUIDEWIRE

(75) Inventors: Satoshi Nagano, Nagoya (JP); Yumiko Nakagawa, Nagoya (JP)

(73) Assignee: Asahi Intecc Co., Ltd., Nagoya-Shi (JP)

( * ) Notice: Subject to any disclaimer, the term of this patent is extended or adjusted under 35 U.S.C. 154(b) by 0 days.

(21) Appl. No.: 13/169,525

(22) Filed: Jun. 27, 2011

(65) Prior Publication Data

US 2012/0041420 A1 Feb. 16, 2012

(30) Foreign Application Priority Data

Aug. 10, 2010 (JP) ................................. 2010-179811

(51) Int. Cl.
*A61M 25/00* (2006.01)
*A61M 25/09* (2006.01)

(52) U.S. Cl.
USPC .......................................... 600/585; 604/528

(58) Field of Classification Search
USPC ..................... 604/187, 528; 600/585
See application file for complete search history.

(56) References Cited

U.S. PATENT DOCUMENTS

| 3,452,742 A | | 7/1969 | Muller | |
|---|---|---|---|---|
| 4,721,117 A | * | 1/1988 | Mar et al. ...................... | 600/585 |
| 4,811,743 A | * | 3/1989 | Stevens ......................... | 600/585 |
| 4,846,186 A | * | 7/1989 | Box et al. ....................... | 600/434 |
| 5,007,434 A | * | 4/1991 | Doyle et al. ................... | 600/585 |
| 5,308,324 A | * | 5/1994 | Hammerslag et al. ......... | 604/528 |
| 5,409,015 A | * | 4/1995 | Palermo ........................ | 600/585 |
| 5,443,448 A | * | 8/1995 | DeVries ..................... | 604/96.01 |
| 5,497,786 A | * | 3/1996 | Urick ............................. | 600/585 |
| 5,636,642 A | * | 6/1997 | Palermo ........................ | 600/585 |
| 5,769,796 A | * | 6/1998 | Palermo et al. ............... | 600/585 |
| 5,876,356 A | * | 3/1999 | Viera et al. .................... | 600/585 |
| 6,139,510 A | * | 10/2000 | Palermo ........................ | 600/585 |
| 6,805,676 B2 | * | 10/2004 | Klint ............................. | 600/585 |
| 6,939,313 B2 | * | 9/2005 | Saadat et al. .................. | 600/587 |
| 7,789,839 B2 | | 9/2010 | Lupton | |
| 2006/0264784 A1 | * | 11/2006 | Lupton ......................... | 600/585 |
| 2010/0324539 A1 | | 12/2010 | Lupton | |

FOREIGN PATENT DOCUMENTS

| EP | 0 739 641 A1 | 10/1996 |
|---|---|---|
| EP | 0 868 924 A2 | 10/1998 |
| EP | 1 525 896 A2 | 4/2005 |

(Continued)

OTHER PUBLICATIONS

Nov. 8, 2011 European Search Report issued in European Patent Application No. EP 11 17 3673.2.

(Continued)

*Primary Examiner* — Emily Schmidt
*Assistant Examiner* — Michael J Anderson
(74) *Attorney, Agent, or Firm* — Oliff & Berridge, PLC

(57) ABSTRACT

A guidewire includes a core shaft and a coil body wound around an outer periphery of the core shaft. A distal end portion of the core shaft and a distal end portion of the coil body is fixed to each other to form a most distal end portion. The coil body includes a linear portion and a bent portion, the linear portion extending in a distal direction from a proximal end of the coil body, the bent portion being provided on a distal side of the liner portion. The core shaft and the coil body located in the bent portion are fixed to each other with a fixing member.

2 Claims, 3 Drawing Sheets

(56) References Cited

FOREIGN PATENT DOCUMENTS

| | | |
|---|---|---|
| JP | B-S44-18710 | 8/1969 |
| JP | A-H06-54911 | 3/1994 |
| JP | A-2007-501648 | 2/2007 |
| WO | WO 2005/014095 | 2/2005 |
| WO | WO 2007/057132 A1 | 5/2007 |

OTHER PUBLICATIONS

Aug. 29, 2012 Office Action issued in Japanese Patent Application No. 2010-179811 (with English-language translation).

* cited by examiner

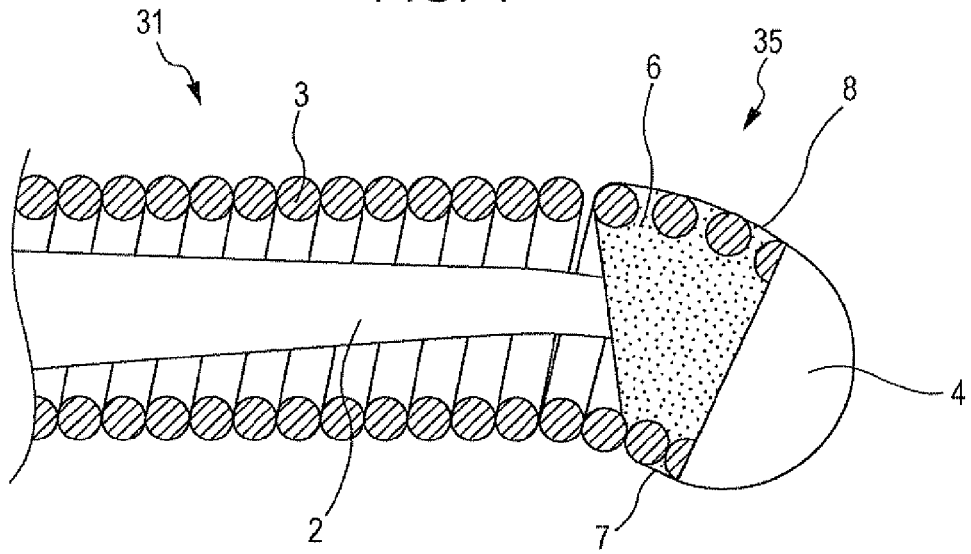
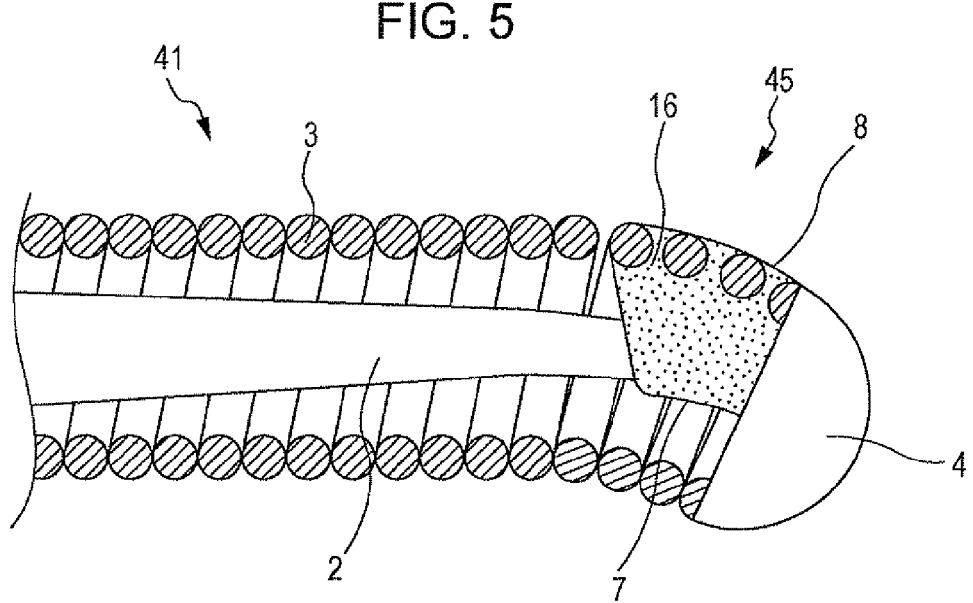

GUIDEWIRE

BACKGROUND OF THE INVENTION

1. Field of the Invention

The present invention relates to a guidewire.

2. Description of the Related Art

To date, various guidewires have been proposed for guiding a medical device to a target region through a body tissue or a tubular organ, such as a blood vessel, an alimentary canal, or a ureter.

For example, Japanese Unexamined Patent Application Publication (Translation of PCT Application) No. 2007-501648 describes a guidewire that includes a core shaft having a rectangular section and having small faces and large faces. The distal end of the core shaft is bent along a central large plane ("central large plane" is a plane that exists between the large faces and that divides the small faces into two) so that the guidewire can be smoothly inserted into a bifurcated vessel.

SUMMARY OF THE INVENTION

However, the guidewire described in Japanese Unexamined Patent Application Publication (Translation of PCT Application) No. 2007-501648 has a problem in that, because the distal end of the core shaft having the small faces and the large faces is bent along the central large plane, the flexural rigidity of the guidewire in a direction perpendicular to the central large plane is low, whereas the flexural rigidity in a direction parallel to the central large plane is increased. As a result, the shape of the bent portion is not stable. Because the shape of the bent portion is not stable, the guidewire has a problem in that the guidewire may not be smoothly inserted into a bifurcated vessel.

The present invention, which has been achieved to address such problems, provides a guidewire that includes a bent portion having a stable shape and that has a high vascular selectivity in a three-dimensional space.

According to an aspect of the invention, a guidewire includes a core shaft; and a coil body formed of a strand that is wound around at least a distal end portion of the core shaft, wherein the coil body includes a linear portion and a bent portion, the linear portion extending in a distal direction from a proximal end of the coil body, the bent portion being provided on a distal side of the liner portion, and wherein at least a part of the bent portion is fixed with a fixing member.

The guidewire according to the aspect of the invention has an advantage in that the guidewire has a high vascular selectivity in a three-dimensional space, because at least a part of the bent portion is fixed with the fixing member and thereby the bent shape of the coil body is stabilized.

BRIEF DESCRIPTION OF THE DRAWINGS

FIG. 4 illustrates an enlarged view of a distal end of a guidewire according to a fourth embodiment of the present invention.

FIG. 5 illustrates an enlarged view of a distal end of a guidewire according to a fifth embodiment of the present invention.

DESCRIPTION OF THE PREFERRED EMBODIMENTS

Hereinafter, guidewires according to embodiments of the present invention will be described with reference to the drawings.

First Embodiment

Figure 1:
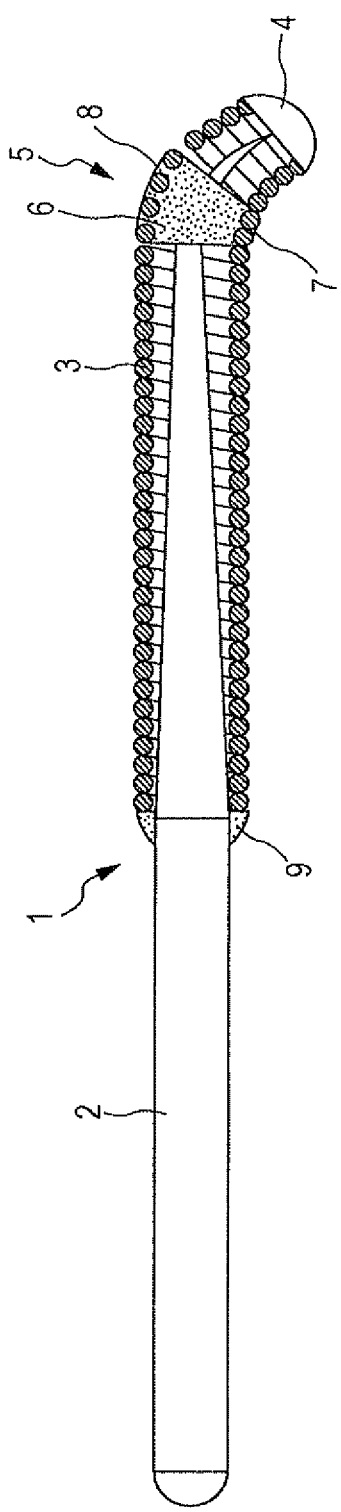
FIG. 1 illustrates an overall view of a guidewire according to a first embodiment of the present invention.

FIG. 1 illustrates an overall view of a guidewire 1 according to a first embodiment of the present invention.

For convenience of description, the left side in FIG. 1 will be referred to as "proximal end" and the right side will be referred to as "distal end". For ease of understanding, the length of the guidewire 1 is reduced and the guidewire 1 is schematically illustrated in FIG. 1. Therefore, the actual dimensions of the guidewire 1 differ from those of FIG. 1.

Referring to FIG. 1, the guidewire 1 includes a core shaft 2 and a coil body 3 that covers a distal end portion of the core shaft 2. The distal end portion of the core shaft 2 and a distal end portion of the coil body 3 are fixed to each other and form a most distal end portion 4. A proximal end portion of the coil body 3 is fixed to the core shaft 2 with a brazed joint 9 at a position between the most distal end portion 4 and a proximal end of the core shaft 2.

The coil body 3 has a linear portion and a bent portion 5. The linear portion extends in the distal direction from the proximal end of the coil body 3. The bent portion 5 is disposed at a position in the distal direction of the liner portion and in the proximal direction of the most distal end portion 4. The core shaft 2 in the bent portion 5 has a bent angle the same as that of the bent portion 5. In the bent portion 5, the coil body 3 and the core shaft 2 are fixed to each other with a fixing member 6.

Adjacent turns of the coil body 3 on an inner arc 7 of the bent portion 5 contact each other and adjacent turns of the coil body 3 on an outer arc 8 of the bent portion 5 do not contact each other.

In this way, the bent portion 5, which is provided in the distal end portion of the guidewire 1, is fixed together with the core shaft 2 and the coil body 3 with the fixing member 6. Therefore, the bent portion 5 having a stable shape can be provided at the distal end of the guidewire 1, whereby the vascular selectivity of the guidewire 1 in a three-dimensional space is improved.

Examples of methods of forming the bent portion 5 include a method of winding a distal end portion of the coil body 3 of the guidewire 1 around a shaping pin, and a method of inserting the coil body 3 and the core shaft 2 into a die having a bent shape and then applying heat to the die. The method of forming the bent portion 5 is not limited to these, and known methods may be appropriately used.

In the present embodiment, the material of the core shaft 2 is not particularly limited. For example, a stainless steel (SUS304), a superelastic alloy such as a Ni—Ti alloy, a piano wire, or the like can be used.

The materials of the most distal end portion 4 and the brazed joint 9, which fix the core shaft 2 and the coil body 3 to each other, are not particularly limited. For example, an aluminum brazing alloy, silver solder, gold solder, zinc solder, a Sn—Pb brazing alloy, a Pb—Ag brazing alloy, a Sn—Ag brazing alloy, or the like can be used.

When fixing the core shaft 2 and the coil body 3 to each other by using such materials, it is preferable that a flux be applied to parts of the core shaft 2 and the coil body 3 on which the most distal end portion 4 and the brazed joint 9 are to be provided. Thus, wettability of a brazing alloy, which is used for the most distal end portion 4 and the brazed joint 9, with the core shaft 2 and the coil body 3 is improved, whereby the strength of fixing is increased.

A radiopaque strand or a radiotransparent strand can be used as the material of the coil body 3. The material of the radiopaque strand is not particularly limited. For example, gold, platinum, tungsten, or an alloy of such metals (for example, a platinum-nickel alloy) can be used. The material of the radiotransparent strand is not particularly limited. For example, a stainless steel (SUS304, SUS316, or the like), a superelastic alloy such as a Ni—Ti alloy, a piano wire, or the like can be used.

A proximal end portion of the coil body 3 may be made of a radiotransparent strand and a distal end portion of the coil body 3 may be made of a radiopaque strand. If a part of the coil body 3 on the distal side of the bent portion 5 is made of a radiopaque strand, an operator can operate the guidewire 1 while watching the bent portion 5 of the guidewire 1, which has a stable shape, by radiography, whereby the vascular selectivity of the guidewire 1 is improved.

In the case where a distal end portion of the coil body 3 on the distal side of the bent portion 5 is made of a radiopaque strand and a proximal end portion of the coil body on the proximal side of the bent portion 5 is made of a radiotransparent strand, it may be necessary, in order to prevent the strands from becoming disconnected, to fix the proximal end of the distal end portion of the coil body 3 and the distal end of the proximal end of the coil body 3 to each other.

Such fixing is performed by temporarily fixing the proximal end of the strand of the distal end portion of the coil body 3 and the strand of the distal end of the proximal end portion of the coil body 3 to each other, forming the bent portion 5 by winding the temporarily fixed strands of the coil body 3 around a pin or the like, and fixing the bent portion 5 with the fixing member 6.

The material of the fixing member 6 is not particularly limited. A synthetic resin or a brazing alloy that is used as the materials of the most distal end portion 4 and the brazed joint 9 can be used. When using the brazing alloy the same as that of the most distal end portion 4 and the brazed joint 9, as described above, it is preferable that a flux be applied to positions of the core shaft 2 and the coil body 3 at which the fixing member 6 is to be provided.

A synthetic resin, which may be used for the fixing member 6, is not particularly limited. A fluorocarbon resin, polyethylene, polypropylene, a polyamide, an elastomer, and a hydrophilic gel can be used.

Second Embodiment

Figure 2:
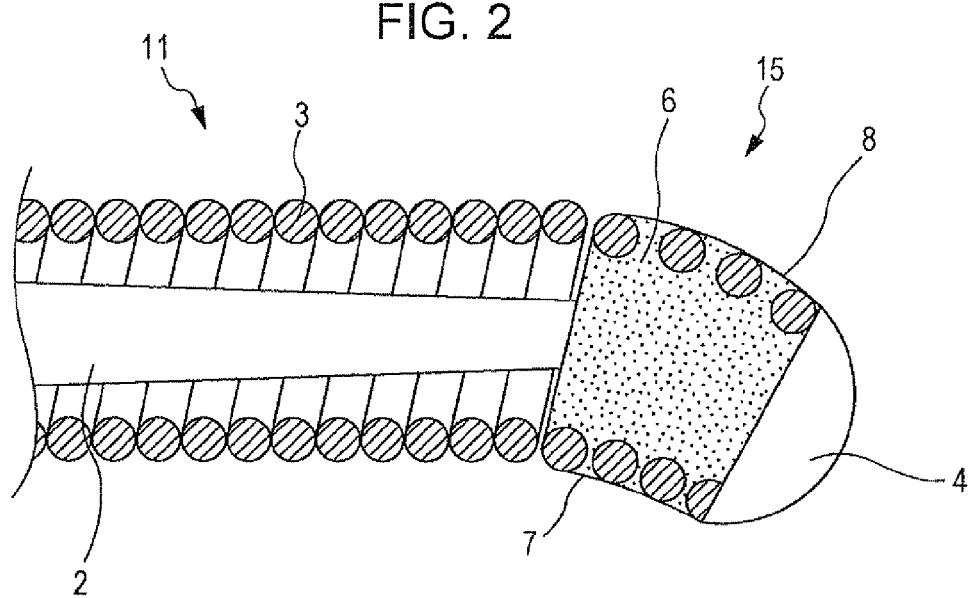
FIG. 2 illustrates an enlarged view of a distal end of a guidewire according to a second embodiment of the present invention.

Referring to FIG. 2, a guidewire 11 according to a second embodiment will be described with emphasis on differences between the second embodiment and the first embodiment. Components of the second embodiment the same as those of the first embodiment will be denoted by the same numerals in FIG. 2. For ease of understanding, only a distal end portion of the guidewire 11 is enlarged in FIG. 2. The length of the guidewire 11 is reduced and the guidewire 11 is schematically illustrated in FIG. 2. Therefore, the actual dimensional ratios of the guidewire 11 differ from those of FIG. 2.

A bent portion 15 of the guidewire 11 is disposed at the proximal end of the most distal end portion 4. Thus, the bent portion 15 has a stable bent shape in a small area from the bent portion 15 to the most distal end portion 4. Therefore, the guidewire 11 having the bent portion 15 has a substantially high vascular selectivity in a three-dimensional space such as a peripheral portion of a coronary artery.

In the present embodiment, there are gaps between adjacent turns of the coil body 3 on the inner arc 7 of the bent portion 15. However, this is not limited thereto, and the adjacent urns may contact each other.

In the present embodiment, the most distal end portion 4 and the fixing member 6 are described as independent members. However, this is not limited thereto, and the most distal end portion 4 and the fixing member 6 may be integrally formed from the same material. By integrally forming the most distal end portion 4 and the fixing member 6 from the same material, the guidewire 11 can be manufactured easily.

Third Embodiment

Figure 3:
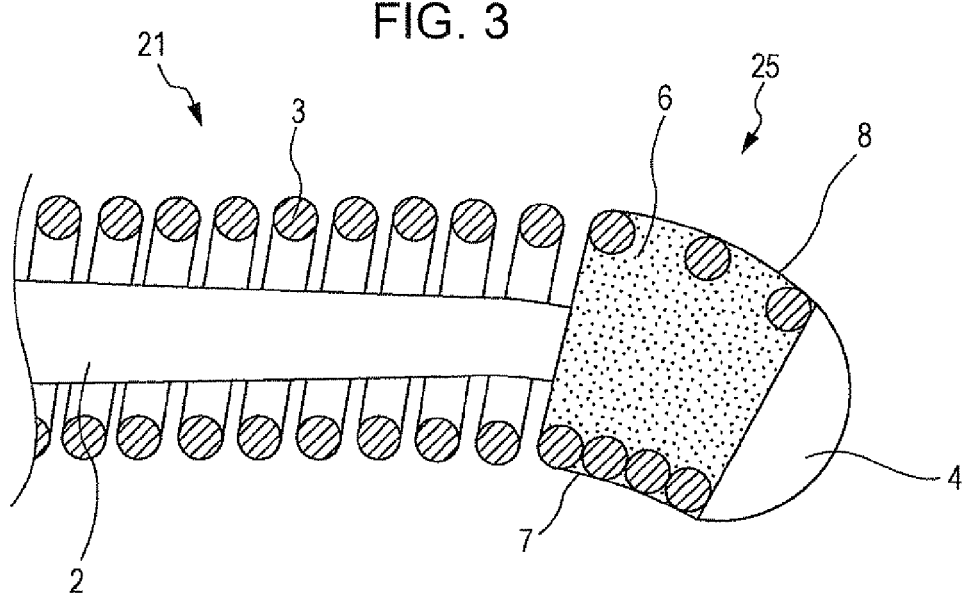
FIG. 3 illustrates an enlarged view of a distal end of a guidewire according to a third embodiment of the present invention.

Referring to FIG. 3, a guidewire 21 according to a third embodiment will be described with emphasis on differences between the third embodiment and the first embodiment. Components of the third embodiment the same as those of the first embodiment will be denoted by the same numerals in FIG. 3. For ease of understanding, only the distal end portion of the guidewire 21 is enlarged in FIG. 3. The length of the guidewire 21 is reduced and the guidewire 21 is schematically illustrated in FIG. 3. Therefore, the actual dimensional ratios of the guidewire 21 differ from those of FIG. 3.

A part of the coil body 3 in the proximal direction of the most distal end portion 4 of the guidewire 21 has a loosely-wound portion. (Because FIG. 3 is an enlarged view of the distal end portion, only the loosely-wound portion of the coil body 3 is illustrated in FIG. 3.) The loosely-wound portion includes the bent portion 25. Adjacent turns of the coil body 3 on the inner arc 7 of the bent portion 25 contact each other, and there are gaps between adjacent turns of the coil body 3 on the outer arc 8 of the bent portion 25. The gaps are larger than the gaps in a part of the loosely-wound portion that is not bent. As the bent portion 25 is formed in the loosely-wound portion, the bent portion 25 has a stable shape having a large bent angle. The guidewire 21 can be inserted into a collateral artery that extends at an obtuse angle from a major artery, such as a coronary artery, and vascular selectivity in a three-dimensional space is substantially improved.

The loosely-wound portion, which includes the bent portion 25, is flexible, so that the flexibility of a part of the guidewire 21 near the bent portion 25 is improved, whereby damage to a blood vessel or other vessels in the body can be prevented.

The bent portion 25, which is formed in the loosely-wound portion, may extend over the entire length of the loosely-wound portion. However, it is preferable that the bent portion 25 extend over a part of the loosely-wound portion. By thus forming the bent portion 25, flexibility of a part of the coil body near the bent portion 25 can be improved.

The widths of the gaps between the turns of the strand in the loosely-wound portion may increase in the distal direction of the coil body 3. In this case, the bent portion 25 can have a larger bent angle, and flexibility of a part the guidewire 21 near the bent portion 25 can be further improved.

When providing two bent portions 25 in the loosely-wound portion, it is preferable that a loosely-wound portion be formed in accordance with each of the bent portions 25. In this case, the guidewire 21 can have a bent shape and flexibility in accordance with the bent shape of each of the bent portions 25.

Fourth Embodiment

Referring to FIG. 4, a guidewire 31 according to a fourth embodiment will be described with emphasis on differences from the first embodiment. Components of the fourth embodiment the same as those of the first embodiment will be denoted by the same numerals in FIG. 4. For ease of understanding, only the distal end portion of the guidewire 31 is enlarged in FIG. 4. The length of the guidewire 31 is reduced and the guidewire 31 is schematically illustrated in FIG. 4. Therefore, the actual dimensional ratios of the guidewire 31 differ from those of FIG. 4.

The fixing member 6 is provided in a bent portion 35 of the guidewire 31. On the inner arc 7 of the bent portion 35, the fixing member 6 fixes two turns of the strand of the coil body 3 to each other. On the outer arc 8 of the bent portion 35, the fixing member 6 fixes four turns of the strand of the coil body 3 to one another. The amount of the fixing member 6 on the inner arc 7 of the bent portion 35 is larger than the amount of the fixing member on the outer arc 8 of the bent portion 35, whereby flexibility of the bent portion 35 of the guidewire 31 can be maintained.

The fixing member 6 can be formed in the bent portion 35 by using the following method.

A method of providing the fixing member 6 in the bent portion 35 includes the steps of, for example, forming the bent portion 35 in the coil body 3 of the guidewire 31, applying a flux to a part of the strand of the coil body 3 located on the inner arc 7 of the bent portion 35 with an amount larger than the amount of flux applied to a part of the strand of the coil body 31 located on the outer arc 8 of the bent portion 35, and making a brazing alloy flow into the bent portion 35 from the outer arc 8 of the strand.

Because the wettability of brazing alloy with the strand is dependent on the amount of flux applied, the number of turns of the strand that are fixed to the fixing member 6 on the inner arc 7 of the bent portion 35 can be made smaller than the number of turns of the strand that are fixed to the fixing member 6 on the outer arc 8 of the bent portion 36. The method of forming the fixing member 6 is not limited to this, and an appropriate known method can be used Fifth Embodiment Referring to FIG. 5, a guidewire 41 according to a fifth embodiment will be described with emphasis on differences from the first embodiment. Components of the fifth embodiment the same as those of the first embodiment will be denoted by the same numerals in FIG. 5. For ease of understanding, only the distal end portion of the guidewire 41 is enlarged in FIG. 5. The length of the guidewire 41 is reduced and the guidewire 41 is schematically illustrated in FIG. 5. Therefore, the actual dimensional ratios of the guidewire 41 differ from those of FIG. 5.

A fixing member 16 is provided in a bent portion 45. The fixing member is provided, not around the entire inner periphery of the coil body 3, but only in a part of the bent portion 45 between the core shaft 2 and the coil body 3 near the outer arc 8 of the bent portion 45. Thus, the fixing member 16 is not present in a part near the inner arc 7 of the bent portion 45, whereby the guidewire 41 has a higher flexibility while maintaining a bent shape.

The fixing member 16 can be made by forming the bent portion 45 and then making the fixing member 16 flow into the bent portion 45 from the outer arc 8 while adjusting the flow amount. When using a brazing alloy as the material of the fixing member 16, by applying a flux only on the outer arc 8 of the bent portion 45 and making the brazing alloy flow into the bent portion 45, the fixing member (brazing alloy) 16 can be formed only in a part of the bent portion 45 near the outer arc 8.

The coil body 3 illustrated in FIG. 1 has only one bent portion 5. However, as a modification, the coil body 3 may have two or more bent portions 5. When providing two or more bent portions, the bent portions may be formed adjacent to each other or may be formed with a distance therebetween in the axial direction.

When providing two bent portions, the direction in which one of the bent portions is bent may be different from the direction in which the other of the bent portions is bent so that the distal end of the guidewire may have a three-dimensional bent shape. Such a guidewire, which has a three-dimensional bent shape at the distal end thereof, has a good insertability into a complicated blood vessel such as a hepatic artery, whereby the vascular selectivity of the guidewire in a three-dimensional space can be improved.

An S-shaped bent shape may be formed by bending one of the bent portions in a direction that is 180° different from the direction in which the other of the bent portions is bent. Such a guidewire, which is S-shaped, has a good insertability into a complicated blood vessel, whereby the vascular selectivity of the guidewire in a three-dimensional space can be improved.

When providing two bent portions, the angle of the bent portion on the proximal end side may be smaller than the angle of the bent portion on the distal end side. In this case, the bent portion on the proximal end side has a smaller bent angle, and the bent potion on the distal end side may a larger bent angle than the bent portion on the proximal end side.

Such a guidewire has a high selectivity of a blood vessel having a large inside diameter because the bent portion on the proximal end side has a smaller bent angle. Moreover, the guidewire has a high selectivity of a blood vessel having a small inside diameter because the bent portion on the distal end side has a bent angle larger than that of the bent potion on the proximal end side. Therefore, the vascular selectivity of the guidewire in a three-dimensional space can be improved.

The number of the bent portions is not limited to two, and may be three or more.

Although not illustrated, a guidewire according to the present invention may further include a linear portion on the distal end side of the bent portion. In the case where the linear portion is provided on the distal end side of the bent portion, the shape of the bent portion is more easily maintained by making a fixing member flow into the bent portion and the linear portion provided on the distal end side of the bent portion and thereby fixing the coil body to the core shaft.

The present invention contains subject matter related to Japanese Patent Application No. 2010-179811 filed in the Japan Patent Office on Aug. 10, 2010, the entire contents of which are incorporated herein by reference.

What is claimed is:

1. A guidewire comprising:
a core shaft;
a coil body formed of a wire that is wound around at least a distal end portion of the core shaft;
a distal fixing member fixing a distal end of the coil body to a distal end of the core shaft, wherein
the coil body includes a bent portion extending in a proximal direction from the distal fixing member and a linear portion extending in a proximal direction from a proximal end of the bent portion; and
a proximal fixing member continuously extending in the proximal direction from the distal fixing member to fix the coil body to the core shaft at the bent portion such that the proximal fixing member causes the coil body to have a stable bent shape at the distal end.

2. The guidewire according to claim 1, wherein
the core shaft has a bent portion extending in a proximal direction from the distal fixing member, the proximal fixing member fixing the bent portion of the coil body to the bent portion of the core shaft so that a direction of the bent portion of the core shaft is substantially similar to a direction of the bent portion of the coil body.

* * * * *